(12) United States Patent
Starr et al.

(10) Patent No.: US 9,066,609 B2
(45) Date of Patent: Jun. 30, 2015

(54) INFANT PATIENT TRANSFER DEVICE

(75) Inventors: Karen P. Starr, Laurel, MD (US); Alexander Flamm, Baltimore, MD (US); Brian Murphy, Baltimore, MD (US); Erik Askin, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 356 days.

(21) Appl. No.: 13/530,279

(22) Filed: Jun. 22, 2012

(65) Prior Publication Data
US 2013/0340770 A1  Dec. 26, 2013

(51) Int. Cl.
| | |
|---|---|
| *A61F 5/37* | (2006.01) |
| *A45F 5/00* | (2006.01) |
| *B68G 5/00* | (2006.01) |
| *A47D 13/02* | (2006.01) |
| *A47D 15/00* | (2006.01) |
| *A61G 1/01* | (2006.01) |
| *A61G 7/10* | (2006.01) |
| *A61M 25/02* | (2006.01) |
| *A45F 3/04* | (2006.01) |

(52) U.S. Cl.
CPC ............... *A47D 13/02* (2013.01); *A61M 25/02* (2013.01); *A61F 5/3776* (2013.01); *A45F 3/04* (2013.01); *A47D 15/008* (2013.01); *A61G 1/01* (2013.01); *A61G 7/1023* (2013.01); *A61G 7/1038* (2013.01); *A61G 2200/14* (2013.01); *A61G 2200/32* (2013.01)

(58) Field of Classification Search
CPC ...................................................... A61G 1/01
USPC .......... 128/870, 869, 846; 224/101, 158, 153, 224/159, 160, 584, 577, 151 R; 5/652, 655, 5/625–629; 600/22, 21; 294/140, 141, 294/142, 156, 150, 155
See application file for complete search history.

(56) References Cited

U.S. PATENT DOCUMENTS

| | | | | |
|---|---|---|---|---|
| 1,462,897 | A | | 7/1923 | Barto |
| 2,551,509 | A | * | 5/1951 | Smith ........................... 294/140 |
| 2,804,249 | A | | 8/1957 | Manalo |
| 3,096,917 | A | * | 7/1963 | Gudiksen ...................... 294/140 |

(Continued)

FOREIGN PATENT DOCUMENTS

| | | |
|---|---|---|
| EP | 0686365 A1 | 12/1995 |
| GB | 635453 A | 4/1950 |

OTHER PUBLICATIONS

Combined Search and Examination Report from GB Application No. 1311045.7 date Nov. 29, 2013.

*Primary Examiner* — Alireza Nia
*Assistant Examiner* — Tarla Patel
(74) *Attorney, Agent, or Firm* — Andrus Intellectual Property Law, LLP

(57) ABSTRACT

A patient transfer device is utilized to transport infant patients between locations within a hospital environment. The patient transfer device includes a center, support section and a pair of side sections that can be moved into contact with each other to surround the infant patient. The first and second side sections each include a handle that can be brought into close proximity to each other and can be grasped by a single hand of a clinician. The patient transfer device includes a stiffening device that is positioned within the center section to provide support for the infant patient during transport. A hold down device is included on one or both of the first and second side sections to securely hold tubes and wires connected to the infant patient during transport of the infant patient.

4 Claims, 4 Drawing Sheets

(56) References Cited

U.S. PATENT DOCUMENTS

| | | | | |
|---|---|---|---|---|
| 3,968,911 A | * | 7/1976 | Haas | 224/158 |
| 4,717,056 A | * | 1/1988 | Carmichael | 224/158 |
| 4,730,759 A | * | 3/1988 | Naidu | 224/158 |
| 4,885,811 A | * | 12/1989 | Hayes | 5/81.1 T |
| 5,333,769 A | * | 8/1994 | Skroski | 224/158 |
| 5,819,341 A | * | 10/1998 | Simantob et al. | 5/98.1 |
| 7,850,595 B2 | * | 12/2010 | White | 600/22 |
| 2008/0313812 A1 | | 12/2008 | Reeves et al. | |
| 2009/0114691 A1 | * | 5/2009 | Bizzell et al. | 224/577 |
| 2011/0021886 A1 | | 1/2011 | Briggs | |
| 2012/0018466 A1 | * | 1/2012 | Topaz et al. | 224/158 |

* cited by examiner

INFANT PATIENT TRANSFER DEVICE

BACKGROUND

The present disclosure generally relates to a device for moving an infant patient. More specifically, the present disclosure relates to an infant transfer device (sling) that can be used to support an infant patient during movement while providing minimal patient stimulation and the required patient support.

Presently, the standard practice used to transfer an infant patient out of an incubator or bed is for a nurse or other care physician to carefully slide a hand (or two) under the infant patient and manually lift the patient. When the nurse physically contacts the infant patient, the patient is often stimulated which, in high risk patients, can introduce unwanted stress to the infant patient. In addition, when a nurse lifts the infant patient, there is an increased risk of the nurse snagging one or more of the multiple lines connected to the patient (IV, EKG leads, ET tube, etc.). The possibility of snagging or disconnecting tubes connected to the infant patient can increase the risk to the infant patient during the lifting procedure.

SUMMARY

The present disclosure relates to a patient transfer device for moving an infant patient. The patient transfer device securely holds the patient and allows a clinician to move the patient utilizing only one hand while providing secure stabilization of the wires and tubes connected to the patient.

The patient transfer device includes a center support section that is positioned beneath the patient. First and second side sections are each connected to the center support section. The first side section includes a first handle while the second side section includes a second handle. When an infant patient is supported on the center support section, the first and second side sections can be moved upward and toward each other such that the first and second handles are positioned in close proximity to each other. When the first and second handles are positioned in close proximity to each other, the clinician can grasp both of the first and second handles with a single hand to move the patient while the patient is supported by the patient transfer device.

The patient transfer device further includes a stiffening device that can be positioned within the center support section to provide rigid support for the infant patient during movement. In one embodiment of the disclosure, the stiffening device is a backboard that is received within a pocket formed in the center support section. The backboard can be selectively removed and inserted onto the center section as needed and desired. The backboard preferably extends along a longitudinal axis, wherein the backboard is flexible along the longitudinal axis and rigid in a direction transverse to the longitudinal axis. The rigid nature of the backboard supports the patient's spine during movement while allowing the first and second side sections to move toward each other to securely envelope the patient during transport.

The patient transfer device may further include a hold down device positioned on one of the first and second side sections. The hold down device receives and retains the wires and tubes connected to the patient such that the wires and tubes are securely retained during transport of the patient. Various types of hold down devices are contemplated as being within the scope of the present disclosure. One embodiment includes a section of material that can be connected to the second side section to hold the tubes and wires in place.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
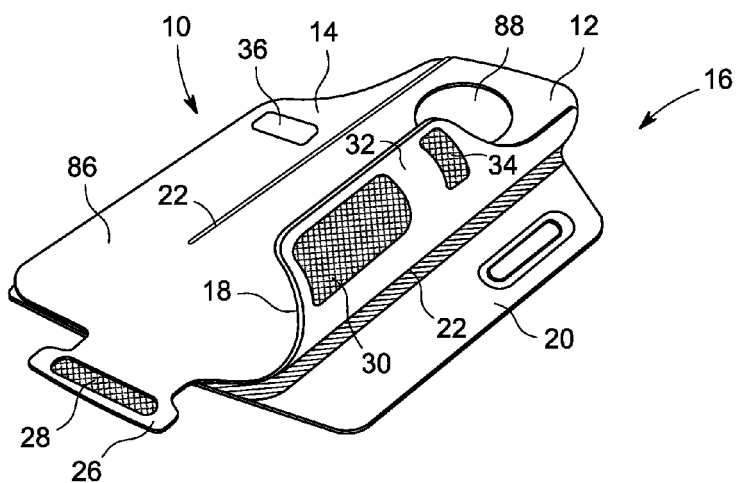
FIG. 1 is a front perspective view of a first embodiment of a patient transfer device of the present disclosure.

FIG. 1 illustrates a patient transfer device 10 of the present disclosure. The patient transfer device 10 can be used to transfer an infant patient from one location to another while minimizing the physical contact between the clinician and the patient while providing secure support for the patient during movement.

Figure 2:
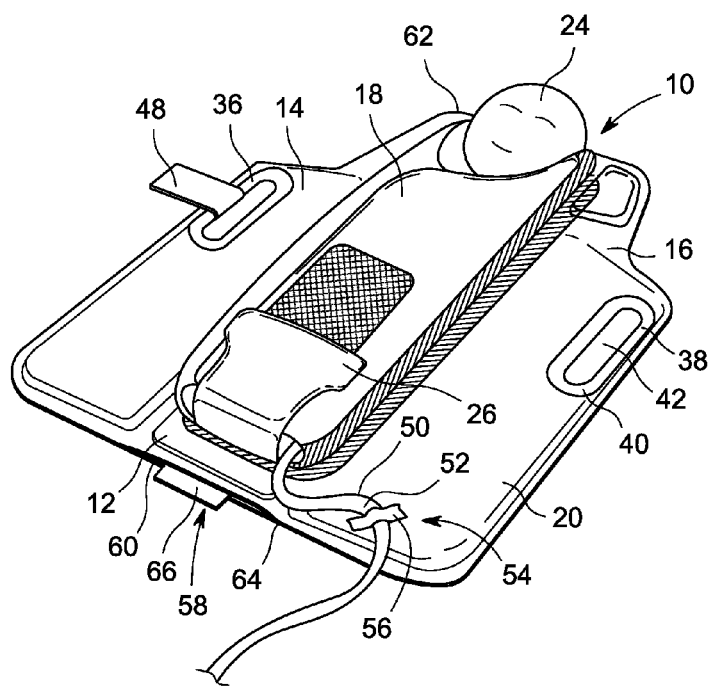
FIG. 2 is a front perspective view of the first embodiment of the patient transfer device with an infant supported on the device.

As illustrated in FIG. 1, the patient transfer device 10 includes a center section 12, a first side section 14 and a second side section 16. In the embodiment illustrated in FIG. 1, the patient transfer device includes an inner liner 18 and an outer liner 20 that each form portions of the center side sections. Although an inner liner 18 and an outer liner 20 are shown as separate components in FIG. 1, it should be understood that the inner and outer liners 18, 20 could be combined as a single layer that forms the center section 12 and the first and second side sections 14, 16. In the embodiment shown in FIG. 1, the inner liner 18 is formed from a soft, foam material and is joined to the outer liner 20 along a pair of spaced attachment lines 22. The outer liner 20 can be formed from a slightly more rigid and durable material as compared to the inner liner 18. As illustrated in FIG. 2, an infant patient 24 can be placed on the inner liner 18 and the opposite sides of the inner liner 18 that forms a portion of the side sections folded over the patient 24 to surround the patient as illustrated.

In the embodiment shown in FIG. 1, the inner liner 18 includes an extended end portion 26 that includes an end fastener 28. When the patient is supported on the inner liner as shown in FIG. 2, the end fastener 28 formed as part of the end portion 26 is received along a second fastener 30. In the embodiment shown in FIGS. 1 and 2, the fasteners 28, 30 are opposite portions of a hook and loop fastener, such as Velcro®. The physical engagement between the fasteners 28, 30 allows the end portion 26 to fold the inner liner 18 in the condition shown in FIG. 2. Although a hook and loop fastener are shown in the embodiment of FIGS. 1 and 2, it should be understood that different types of fasteners could be utilized while operating within the scope of the present disclosure. Alternatively, the end portion 26 could be eliminated while also operating within the scope of the present disclosure.

Referring back to FIG. 1, the fastener 30 is secured to an inner surface 32 of the inner liner 18 and is exposed only after the second side section of the inner liner is wrapped around the infant patient. In addition to the fastener 30, an upper fastener portion 34 is also positioned along the inner surface 32. The upper fastener portion 34 is engaged by a mating fastener 36 formed along the first side section 14 of the inner liner 18. The fasteners 34, 36 can also be mating portions of a hook and loop fastener, such as Velcro®. The fasteners 34, 36 aid in holding the first and second side sections of the inner liner 18 in the condition shown in FIG. 2. Although hook and loop fasteners are shown in the embodiment of FIGS. 1 and 2, it should be understood that other types of fasteners could be utilized while operating within the scope of the present disclosure.

As illustrated in FIG. 2, the portion of the outer liner 20 that forms a portion of the first side section 14 includes a first handle 36 while the portion of the outer liner 20 that forms a portion of the second side portion 16 includes a second handle 38. In the embodiment shown in FIG. 2, the first and second handles 36, 38 are formed only in the outer liner 20 and are defined by a plastic outer housing 40 that forms an open interior 42.

Figure 3:
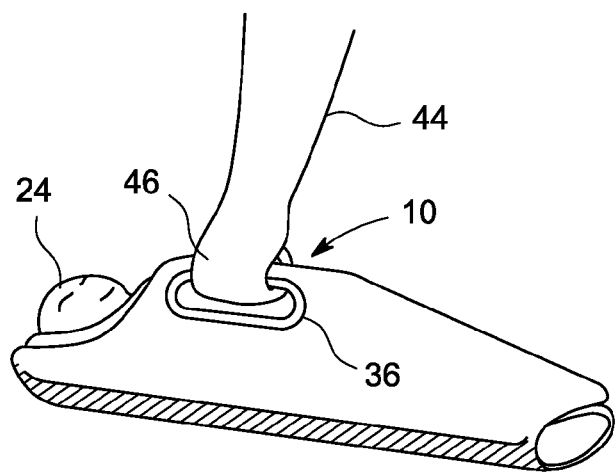
FIG. 3 is a view illustrating the use of the transfer device to move an infant patient.

As can be seen in FIG. 3, when the infant patient 24 is supported along the transfer device 10, a clinician 44 can grasp the pair of handles 36, 38 with a single hand 46 and lift the infant patient for transport and movement. As can be understood in FIGS. 2 and 3, the first and second side sections 14, 16 are sized such that the first and second handles 36, 38 are located close enough to each other to facilitate grasping of the entire patient transfer device 10 by the single hand 46.

Referring back to FIG. 2, in the embodiment illustrated, a strap 48 can be attached to one of the first and second handles 36, 38 and used to secure the handles together during transport of the patient 24. Although a flexible strap 48 is shown in FIG. 2, various other types of straps could be utilized while operating within the scope of the present disclosure. Alternatively, the strap 48 could be eliminated.

Figure 4:
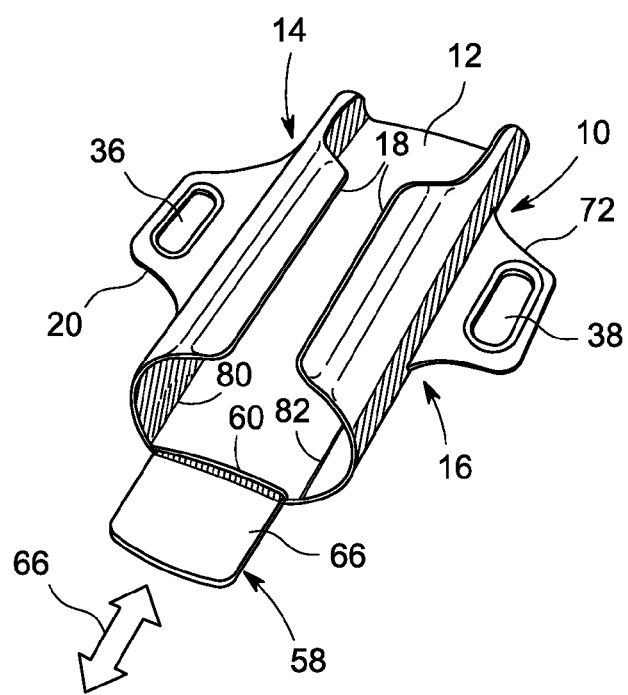
FIG. 4 is a front perspective view of a second, alternate embodiment of the patient transfer device.

As illustrated in FIG. 2, a series of tubes 50 and wires 52 are often attached to the patient 24 that needs to be transported. Since the wires and tubes 50, 52 are often inserted into the patient or connected at specific locations on the patient, it is desirable not to disrupt the tubes and wires during movement. Thus, a need exists for some type of hold down device to prevent the tubes and wires from being disconnected from the patient 24 during transport. In the embodiment shown in FIG. 2, a hold down device 54 is formed on one of the first and second side sections 14, 16 of the transport device. In the embodiment of FIG. 4, a section of adhesive tape 56 is attached to the inner surface of the outer liner 20 in the second side section 16. Although adhesive tape 56 is shown in FIG. 2, other types of hold down devices 54 are contemplated as being within the scope of the disclosure. For example, the hold down device 54 could be a section of a hook and loop fastener, a strap with a button on snap, a section of flexible material or any other type of device that could be utilized to hold the tubes and wires 50, 52 in a secure position as illustrated.

In the embodiment shown in FIG. 2, a stiffening device 58 is shown inserted into a pocket 60 formed in the center section 12 of the patient transfer device 10. The stiffening device 58 typically extends the entire length of the center section 12 from the first end 62 near the patient's head to a second end 64 near the feet of the patient. The stiffening device 58 provides the required stiffness for the patient transfer device 10 such that when the patient transfer device 10 is used to support the patient, the stiffening device 58 prevents the first and second side sections 14, 16 from collapsing onto the patient 24. Additionally, the stiffening device 58 provides the required stiffness for the transfer device 10 such that the transfer device and the patient do not collapse in the longitudinal direction between the first end 60 and the second end 62.

In the embodiment shown in FIGS. 1 and 2, the stiffening device 58 is a backboard that is received within the pocket 60 and extends the entire length of the patient transfer device 10 from the first end 62 to the second end 64. The backboard 66 is preferably formed from a plastic material that has the required stiffness, durability and size to provide the required support for the infant patient 24. Although plastic is described as being the most preferred material for the backboard 66, it is contemplated that other materials could be utilized while operating within the scope of the present disclosure.

Alternatively, the removable stiffening device 58 and sewn-in pocket 60 could be replaced with other types of stiffening devices. As an example, a series of inflatable tubes could be formed within the center section 12 and selectively inflated/deflated depending upon whether the patient 24 is on the transfer device 10 and needs to be moved. Various other types of stiffening devices are also contemplated as being within the scope of the present disclosure. The use of the stiffening device 58 is contemplated as being valuable to provide secure and stable support for the infant patient 24 during movement.

Figure 5:
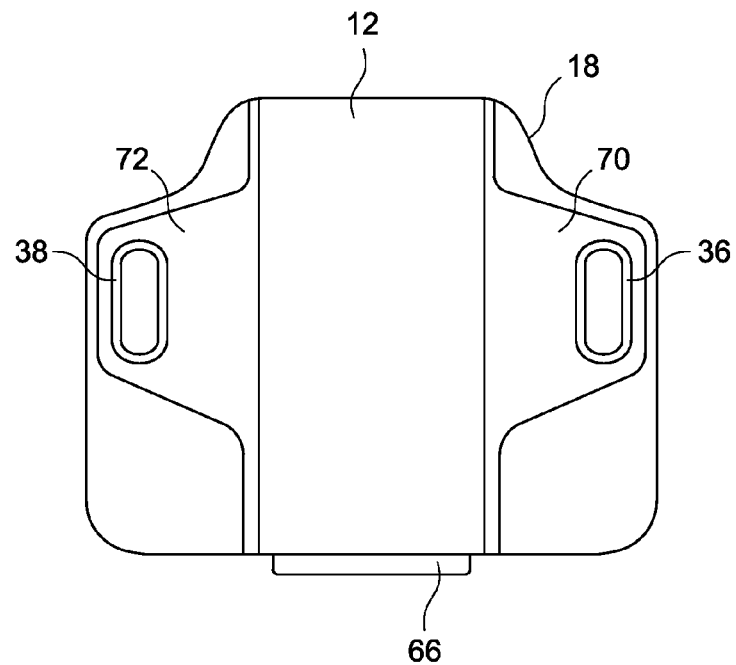
FIG. 5 is a back view of the patient transfer device.

FIGS. 4 and 5 illustrate a second embodiment of the patient transfer device 10 of the present disclosure. In the second embodiment shown in FIGS. 4 and 5, the stiffening device 58 is also a backboard 66 that can be moved in the direction shown by arrows 68 into and out of a pocket 60 formed in the center section 12. In the embodiment shown in FIG. 4, the first side section 14 includes the inner liner 18 and a smaller, outer liner 70. Likewise, the second side section 16 includes the inner liner 18 and smaller, outer liner 72. The outer liners 70, 72 include the first and second handles 36, 38 as in the first embodiment shown in FIGS. 1-2.

Figure 6:
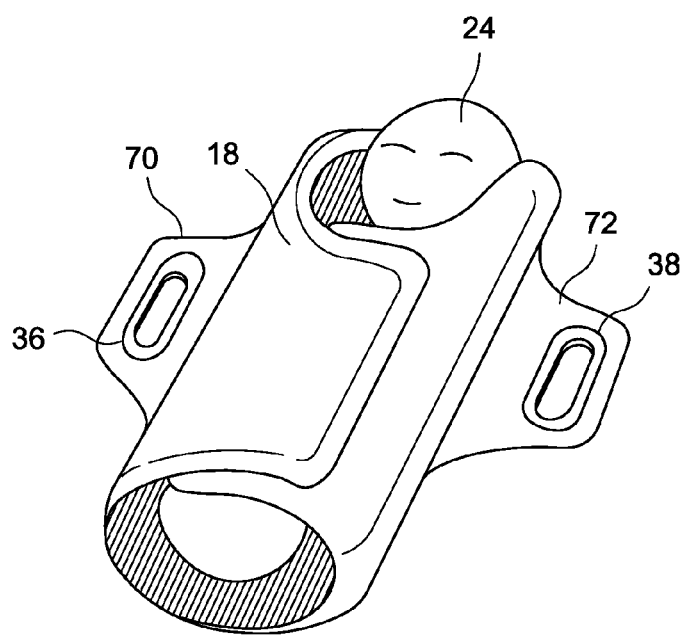
FIG. 6 is a view of the alternate embodiment of the patient transfer device used to support an infant patient.
Figure 7:
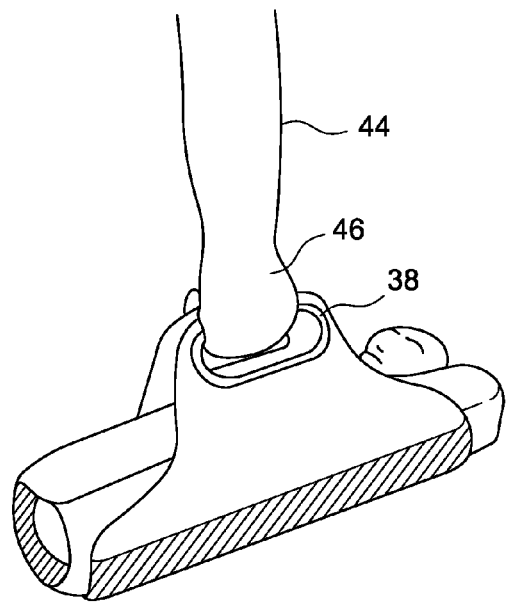
FIG. 7 is a view showing the transport of an infant patient using the transfer device of the present disclosure.

As illustrated in the back view of FIG. 5, the outer liner sections 70, 72 are joined to the center section 12. As in the first embodiment, the inner liner 18 is formed from a soft, foam material that provides a comfortable support surface for an infant patient when the infant patient is supported on the inner liner 18. As illustrated in FIG. 6, the patient 24 is supported along the center section and the inner liner of both the first and second side sections are wrapped around the patient 24. Although not illustrated, it is contemplated that various types of fastening devices and materials could be utilized to hold the opposite sides of the inner liner 18 in place as shown. When the patient 24 is wrapped within the inner liner 18 as illustrated, the outer liner sections 70, 72 of the first and second side sections can be brought together such that a single hand 46 of the clinician 44 can be used to grasp both handles, as illustrated in FIG. 7.

Figure 8:
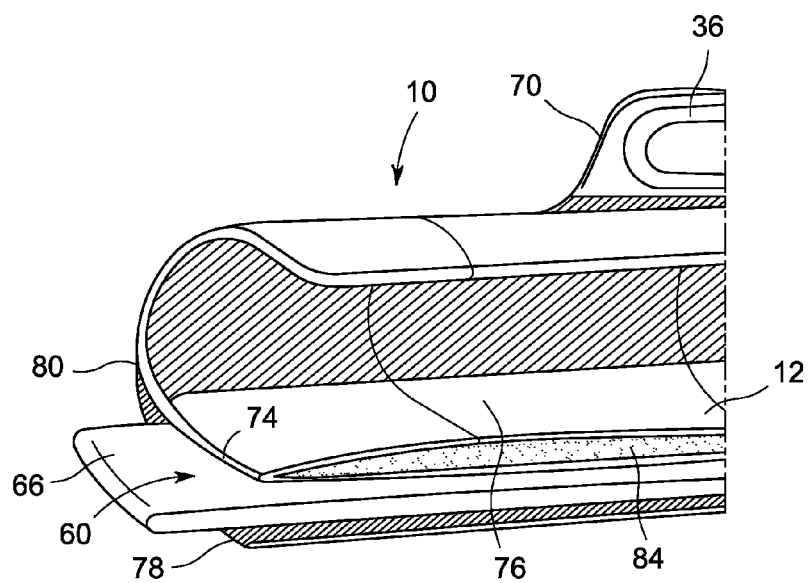
FIG. 8 is a partial section view illustrating the insertion of the backboard within the transfer device.

FIG. 8 provides a section view of the composition and materials used to form the patient transfer device 10 shown in the embodiment of FIGS. 4 and 5. As illustrated, the patient transfer device 10 includes a center section 12. The center section includes a first layer 74 that defines an inner surface 76 that comes in direct contact with the infant patient when the infant patient is supported on the patient transfer device. A second layer of material 78 is attached to the first layer 74 at an attachment point 80. As illustrated in FIG. 4, the second layer 78 is also attached to the first layer at a second attachment line 82. As illustrated in FIG. 8, the second layer 78 is not attached to the first layer 74 between the pair of spaced attachment lines 80, 82 to define the open pocket 60. The open pocket 60 extends along the entire length of the patient transfer device 10 from the first end to the second end. As illustrated in FIG. 4, the backboard 66 can be removably received from within the pocket 60.

In the embodiment shown in FIG. 8, a layer of foam 84 is contained within the first layer 74 to provide additional cushioning for the patient when the patient is supported by the patient transfer device 10.

Referring back to FIGS. 1 and 2, the method of utilizing the patient transfer device 10 of the present disclosure will now be described. Although the present method is being described as one preferred method of utilizing the patient transfer device 10, it should be understood that the patient transfer device 10 could be utilized in different ways depending upon the clinician requirement and the desired amount of movement necessary for the patient 24.

Initially, the patient transfer device 10 is positioned within an incubator or patient bed before the patient is placed within the incubator or bed. It is contemplated that the patient transfer device 10 could be placed in an incubator in situations in which the patient will be moved frequently by the clinician.

Once the patient transfer device 10 is placed within the incubator, the patient is placed on the outer surface 86 of the inner layer 18 in the center section 12. In the embodiment illustrated, the inner layer 18 includes a headrest 88 that includes additional cushioning for the patient's head. However, the headrest 88 could be eliminated while operating within the scope of the present disclosure.

When it is desired to move the patient 24, the clinician initially installs or activates the stiffening device 58 within the center section 12. In the embodiment shown in FIG. 2, the stiffening device 58 is a backboard 66 which is inserted into the open pocket 60 formed in the center section 12. Although a backboard 66 is shown in the embodiment, other types of stiffening devices could be utilized while operating within the scope of the present disclosure. It is desirable that the stiffening device 58 can be selectively removed to increase the comfort of the patient 24 if simply resting within a bed or incubator.

As described previously, it is desired that the backboard 66 be inflexible in a direction transverse to the lengthwise, longitudinal axis of the backboard 66. The rigid, inflexibility of the backboard 66 in a direction transverse to the longitudinal axis provides additional support for the back and spine of the patient during transport. However, it is also desirable that the backboard 66 be somewhat flexible toward the longitudinal axis so that when the first and second side sections are lifted over the patient, the backboard slightly flexes to increase the comfort for the patient.

Once the stiffening device 58 has been positioned in the center section 12, the inner layer that defines the first side section 14 is folded upward and into contact with the patient. Once in place, the portion of the inner layer defining the second side section 16 is folded into contact with the opposite side of the inner layer and the first and second fasteners 34, 36 engage each other to hold the inner layer in the condition shown in FIG. 2.

Once the first layer is folded into the condition shown in FIG. 2, the end portion 26 is folded upward into contact with the fastener 30. At this time, the wires and tubes leading from the patient are securely attached to the second side section 16 utilizing the hold down device 54. Although the hold down device 54 is shown positioned on the second side section 16, it should be understood that the hold down device 54 could also be on the first side section 14 or a separate hold down device included on each of the first and second side sections 14, 16.

Once the wires and tubes 50, 52 have been secured by the hold down device 54, the first and second side sections 14, 16 are brought upward toward each other until the first handle 36 and the second handle 38 are positioned near each other. Once the first and second handles are positioned near each other, the handles can be grasped by a single hand 46 of the clinician, as shown in FIG. 4. When in this position, the backboard 66 provides secure support for the patient 24.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A transfer device for supporting an infant patient during movement of the infant patient, comprising:
   a center support section positionable beneath the infant patient, the center support section including a receiving pocket;
   a stiffening device positioned within the receiving pocket of the center support section to provide support for the infant patient during movement, wherein the stiffening device is a removable backboard extending along a longitudinal axis, wherein the backboard is flexible along the longitudinal axis and rigid in a direction transverse to the longitudinal axis;
   a first side section connected to the center support section and including a first handle; and
   a second side section connected to the center support section and including a second handle, wherein the first and second side sections are movable toward each other such that the first and second handles are located adjacent to each other and the first and second side sections surround the infant patient.

2. The transfer device of claim 1 wherein the center support section and the first and second side sections are formed as a single unit.

3. The transfer device of claim 1 wherein at least one of the first and second side sections includes a hold down device configured to receive and secure tubes and wires attached to the patient.

4. The transfer device of claim 1 further comprising an attachment device to join the first and second side sections.

* * * * *